US007265233B2

(12) United States Patent
Kawano et al.

(10) Patent No.: US 7,265,233 B2
(45) Date of Patent: Sep. 4, 2007

(54) ORGANOMETALLIC IRIDIUM COMPOUND, PROCESS FOR PRODUCING THE SAME AND PROCESS FOR PREPARING FILM

(75) Inventors: Kazuhisa Kawano, Ebina (JP); Mayumi Takamori, Sagamihara (JP); Noriaki Oshima, Yokohama (JP)

(73) Assignees: Tosoh Corporation, Yamaguchi (JP); Sagami Chemical Research Center, Kanagawa (JP)

( * ) Notice: Subject to any disclaimer, the term of this patent is extended or adjusted under 35 U.S.C. 154(b) by 18 days.

(21) Appl. No.: 10/568,388

(22) PCT Filed: Aug. 11, 2004

(86) PCT No.: PCT/JP2004/011796

§ 371 (c)(1),
(2), (4) Date: Feb. 15, 2006

(87) PCT Pub. No.: WO2005/017950

PCT Pub. Date: Feb. 24, 2005

(65) Prior Publication Data

US 2006/0204660 A1     Sep. 14, 2006

(30) Foreign Application Priority Data

| Aug. 19, 2003 | (JP) | ............................... 2003-295329 |
| Nov. 12, 2003 | (JP) | ............................... 2003-383169 |
| Jan. 13, 2004 | (JP) | ............................... 2004-005503 |

(51) Int. Cl.
C07F 17/02     (2006.01)
C07F 15/00     (2006.01)
C23C 16/00     (2006.01)
(52) U.S. Cl. ...................................... 556/136; 427/252
(58) Field of Classification Search ................ 556/136; 427/252
See application file for complete search history.

(56) References Cited

U.S. PATENT DOCUMENTS 4,670,621 A     6/1987     Walker (Continued)

OTHER PUBLICATIONS

International Search Report dated Feb. 1, 2005.
M. Dziallas, et al., Basische Metalle LXII Darstellung Und Reaktionen Dermetall-Basen $C_5H_5Ir$ (OLEFIN) $PPr_3$ Und $C_5H_5Ir$ (OLEFIN)$_2$, Journal of Organometallic Chemistry, 1987, vol. 330, No. 1-2, pp. 207-219.

(Continued)

*Primary Examiner*—Porfirio Nazario-Gonzalez
(74) *Attorney, Agent, or Firm*—Sughrue Mion PLLC

(57) ABSTRACT

An organometallic iridium compound having low melting point, excellent vaporization characteristic and low film formation temperature on a substrate, a process for producing the compound, and a process for preparing iridium-based films using the organometallic compound are provided.

The organometallic iridium compound represented by the formula (1)

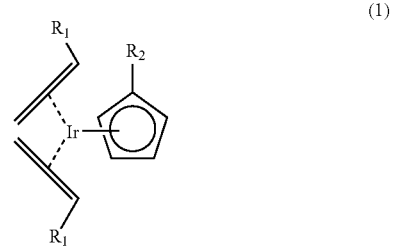

(1)

(example of specific compound: (ethylcyclopentadienyl)bis (ethylene)iridium) is obtained by reacting a compound represented by the formula (4)

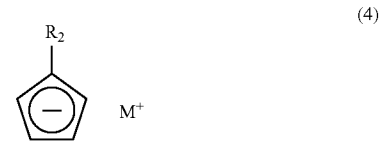

(4)

with a compound represented by the formula (2) or (3)

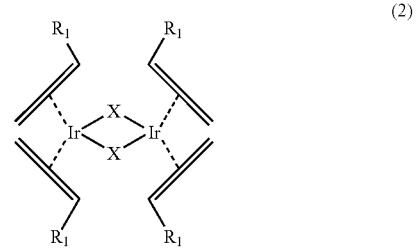

(2)

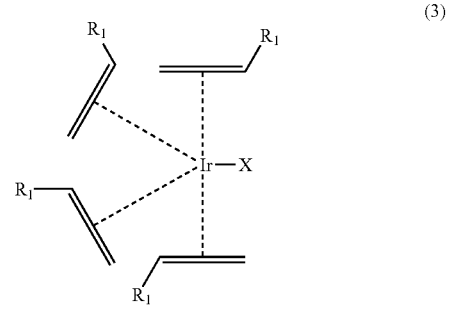

(3)

An iridium-based film is prepared using the compound as a precursor. In the formulae, $R_1$ represents hydrogen atom or a lower alkyl group; $R_2$ represents a lower alkyl group; X represents a halogen atom; and M represents an alkali metal.

6 Claims, 3 Drawing Sheets

U.S. PATENT DOCUMENTS

| | | |
|---|---|---|
| 4,751,344 A | 6/1988 | Walker |
| 4,992,305 A | 2/1991 | Erbil |
| 5,130,172 A | 7/1992 | Hicks et al. |
| 6,319,832 B1 | 11/2001 | Uhlenbrock et al. |
| 6,884,902 B2 | 4/2005 | Takamori et al. |
| 2001/0031539 A1 | 10/2001 | Uhlenbrock et al. |
| 2004/0215029 A1* | 10/2004 | Takamori et al. ........... 556/136 |

OTHER PUBLICATIONS

A. L. Onderdelinden, et al., "Chloro- and Bromo- (alkene)iridium (I) Complexes", Inorganica Chimica Acta, 6:3, Sep. 1972.

* cited by examiner

ORGANOMETALLIC IRIDIUM COMPOUND, PROCESS FOR PRODUCING THE SAME AND PROCESS FOR PREPARING FILM

TECHNICAL FIELD

The present invention relates to an organometallic compound that can be a precursor for preparing iridium-based films on substrates, a process for producing the compound, and a process for preparing iridium-based films.

BACKGROUND ART

In integrated circuits in recent years, ferroelectric memories using residual polarization of ferroelectrics are eagerly investigated. Specifically, lead zirconate titanate (PZT: $Pb(Ti, Zr)O_3$), strontium bismuth tantalate (SBT: $SrBi_2Ta_2O_9$), and the like are investigated. As electrode materials of those ferroelectrics, noble metal thin films of ruthenium, platinum, iridium, and the like, or oxide thin films of these noble metals become necessary. In particular, iridium and iridium oxide are considered to be a leading part of electrode materials in the future. As the production process of iridium and iridium oxide thin films, a sputtering process and a chemical vapor deposition process (CVD process) are employed. In particular, the CVD process is considered as the mainstream in the production process of thin film electrodes in the future for the following reason. The CVD process is liable to produce uniform films, and also has excellent step coverage, and therefore, this process can be compatible with higher density formation to the recent circuits and electronic parts.

As precursors for forming thin films using this CVD process, it is considered that among metallic compounds, organometallic compounds that have low melting point and are easy to handle are suitable. Hitherto, tris(dipivaloylmethanato)iridium, tris(acetylacetonato)iridium, (cyclopentadienyl)(1,5-cyclooctadiene)iridium, and the like have been investigated as an organometallic compound for the purpose of depositing an iridium or iridium oxide thin film. Those iridium compounds have high stability in the atmosphere and are non-toxic, and therefore, have aptitude as a precursor of CVD. However, those iridium compounds are solid at ordinary temperatures and involve such a problem that vaporization of the precursor and transportation to a substrate are difficult.

In recent years, iridium complexes having a low melting point are eagerly investigated. As a measure of making the iridium complexes have a low melting point, there is a measure to form a compound in which at least one hydrogen atom on a cyclopentadienyl ring in cyclopentadienyl(1,5-cyclooctadiene)iridium is substituted with an alkyl group.

For example, as cyclopentadienyl derivatives, (1,5-cyclooctadiene)(ethyl-cyclopentadienyl)iridium is disclosed (for example, JP-A-11-292888). Since this metallic compound is liquid at ordinary temperatures, and its melting point is low as compared with that of(cyclopentadienyl)(1, 5-cyclooctadiene)iridium, it is considered that this compound is possessed of characteristics necessary as the precursor applied to the CVD process. However, this compound has extremely high stability, and the decomposition temperature of the complex is high. Accordingly, it is inevitably required to increase the substrate temperature at the time of film formation. As a result, there is encountered such a problem that the step coverage at the time of film-formation is poor. There is further encountered such a problem that an iridium oxide film is difficult to be formed. In the meanwhile, as a report of iridium complexes having ethylene and cyclopentadienyl group as regards, there is a synthesis example of (cyclopentadienyl)bis(ethylene)iridium (for example, see M. Dziallas, A. Hohn and H. Werner, *J. Organomet. Chem.*, 330 (1987) 207-219). However, the compound is solid at room temperature and is not suitable as a CVD precursor.

DISCLOSURE OF THE INVENTION

The present invention has been made in view of the above technical problems. That is, the present invention relates to an organometallic compound that can be a precursor for preparing iridium-based films, and the objects are to provide the organometallic compound having a low melting point, excellent vaporization characteristics and low film formation temperature on a substrate, a process for producing the same, and a process for preparing iridium-based films using the organometallic compound.

The present inventors have made extensive and intensive investigations to solve the above-described problems. As a result, a novel iridium complex exhibiting a melting point such that it is liquid at room temperature and having good vaporization characteristics and decomposition characteristics has been developed by introducing a lower alkyl group into a cyclopentadienyl ring (hereinafter referred to as "Cp ring") or ethylene of (cyclopentadienyl)bis(ethylene)iridium.

The present invention provides an organometallic iridium compound represented by the following general formula (1):

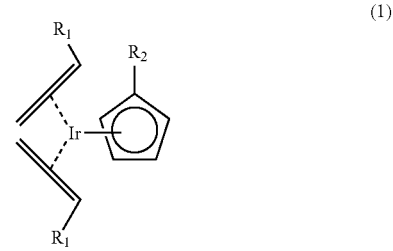

(1)

wherein $R_1$ represents hydrogen atom or a lower alkyl group; and $R_2$ represents a lower alkyl group.

The present invention further provides a process for producing the organometallic iridium compound represented by the general formula (1), which comprises reacting a compound represented by the following general formula (4):

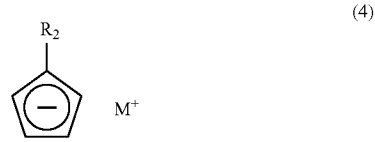

(4)

wherein $R_2$ represents a lower alkyl group, and M represents an alkali metal, with a compound represented by the following general formula (2) or a compound represented by following general formula (3):

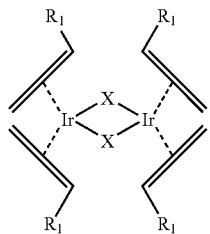

(2)

wherein $R_1$ is the same as defined above, and X represents a halogen atom,

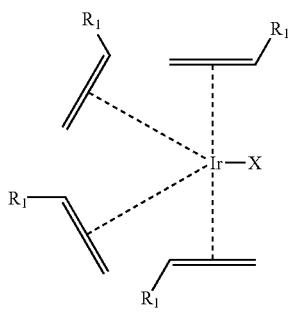

(3)

wherein $R_1$ and X are the same as defined above.

The present invention further provides a process for preparing iridium-based films, which comprises using, as a precursor, the organometallic iridium compound represented by the general formula (1).

Figure 1:
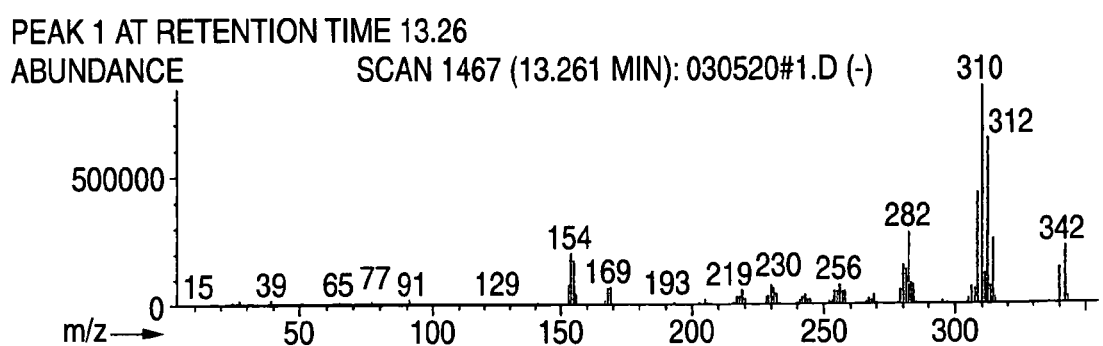
FIG. 1 is a view showing GC/MS chart of the iridium compound obtained in Example 1.

In the drawings:
1: Precursor container
2: Oil bath
3: Reaction chamber
4: Substrate
5: Oxidation gas
6: Counter gas
7: Carrier gas
8: Mass flow controller
9: Mass flow controller
10: Mass flow controller
11: Vacuum pump
12: Exhaust

BEST MODE FOR CARRYING OUT THE INVENTION

The present invention is described in detail below.

Definition of the terms used in the present specification and specific examples thereof will be described.

The term "lower alkyl group" used herein means a straight-chain, branched or cyclic alkyl having 1-6 carbon atoms. Therefore, examples of the lower alkyl group used in $R_1$ and $R_2$ include methyl, ethyl, n-propyl, isopropyl, n-butyl, isobutyl, sec-butyl, tert-butyl, pentyl, isopentyl, neopentyl, tert-pentyl, 1-methylbutyl, 2-methylbutyl, 1,2-dimethylpropyl, hexyl, isohexyl, 1-methylpentyl, 2-methylpentyl, 3-methylpentyl, 1,1-dimethylbutyl, 2,2-dimethylbutyl, 1,3-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl, cyclopropyl, cyclobutyl, cyclopentyl, cyclohexyl, cyclopropylmethyl, 1-cyclopropylethyl, 2-cyclopropylethyl, and cyclobutylmethyl.

In the present invention, $R_1$ represents hydrogen atom or a lower alkyl group. $R_1$ is preferably methyl or hydrogen atom, and more preferably hydrogen atom. On the other hand, in the present invention, $R_2$ represents a lower alkyl group. The lower alkyl group is preferably methyl, ethyl, propyl or butyl, and more preferably methyl or ethyl. In the present invention, X represents a halogen atom. Examples of the halogen atom include fluorine, chlorine, bromine and iodine. Of those, chlorine or bromine is preferable. In the present invention, M represents an alkali metal. Examples of the alkali metal include lithium, sodium and potassium. Of those, lithium or sodium is preferable.

The organometallic iridium compound represented by the general formula (1) of the present invention can be obtained by reacting the compound represented by the general formula (4) with the compound represented by the general formula (2) or the compound represented by the general formula (3). Reaction conditions in such a reaction are not particularly limited. For example, the two compounds each may be added to appropriate solvents, respectively, and the respective solutions may be mixed and reacted at low temperature. Post-treatment is not particularly limited. Generally employed method is that a mixed solution after completion of the reaction is concentrated; the desired compound is extracted from the resulting mixture using an organic solvent such as pentane, hexane or ether; an appropriate carrier is selected; the extract is subjected to column chromatography using the appropriate solvent as an eluant; and the extract is subjected to distillation. Thus, the desired organometallic iridium compound can be obtained.

An iridium-based film can be produced using, as the precursor, the organometallic iridium compound represented by the general formula (1) of the present invention. Specific means for such a production process is not particularly limited. For example, any of CVD process, atomic layer deposition process (ALD process), and spin coating process may be used.

In the case of producing the iridium-based film by CVD process, ALD process or the like using the organometallic iridium compound represented by the general formula (1) of the present invention, a method of supplying the precursor to a film-formation chamber is not particularly limited. For example, a bubbling process may be used, and a liquid injection process may also be used.

In the present invention, in the case of producing the iridium-based film by CVD process or ALD process, the organometallic iridium compound may be used as it is, or may be dissolved in an organic solvent and then used as an organometallic iridium compound solution.

Examples of the organic solvent that is used in the case of using as a solution include alcohols (for example, methanol, ethanol or isopropanol), esters (for example, ethyl acetate, butyl acetate or isoamyl acetate), glycol ethers (for example, ethylene glycol monoethyl ether, ethylene glycol monomethyl ether or ethylene glycol monobutyl ether), ethers (for example, diethyl ether, glyme, diglyme, triglyme or tetrahydrofuran), ketones (for example, methyl butyl ketone, methyl isobutyl ketone, ethyl butyl ketone, dipropyl ketone, diisobutyl ketone, methyl amyl ketone or cyclohexanone), and hydrocarbons (for example, hexane, cyclohexane, ethylcyclohexane, heptane, octane, benzene, toluene or xylene). However, the present invention is not limited to those.

EXAMPLE

The present invention is described in more detail by reference to the following Examples, but it should be understood that the invention is not construed as being limited thereto.

Example 1

Synthesis and Thermal Decomposition Characteristic of (ethylcyclopentadienyl)bis-(ethylene)iridium:

49 mg of di μ-chlorotetrakis(ethylene)diiridium (I) was added to 10 ml of THF, and a reaction flask was cooled to −78° C., to which 10 ml of a THF solution of 17 mg of lithium ethylcyclopentadienide was then added. The resulting mixture was stirred at −78° C. for 30 minutes, the temperature was then gradually elevated to room temperature, and the resulting mixture was further reacted for 1 hour, followed by concentration to obtain a muddy mixture. The muddy mixture was subjected to extraction with hexane, and the extract solution was subjected to column chromatography (eluant: hexane) using alumina to obtain 14 mg of the desired (ethylcyclopentadienyl)bis(ethylene)iridium.

Pale Yellow Oily Material $^1$H-NMR (500 MHz, Benzene-d6, δ ppm): 4.78-4.77 (m, 2H), 4.66-4.65 (m, 2H), 2.60-2.58 (m, 4H), 1.90 (q, J=2.5 Hz, 2H), 0.94 (t, J=2.5 Hz, 3H), 0.94-0.91 (m, 4H) IR (neat, cm$^{-1}$): 3040, 2970, 2920, 2870, 1480, 1460, 1435, 1310, 1165, 1150, 1035, 1010, 990, 810, 790 MS (GC/MS, EI): Molecular ion peak of (ethylcyclopentadienyl)bis(ethylene) iridium in terms of $^{193}$Ir: m/z 342 (FIG. 1)

Figure 2:
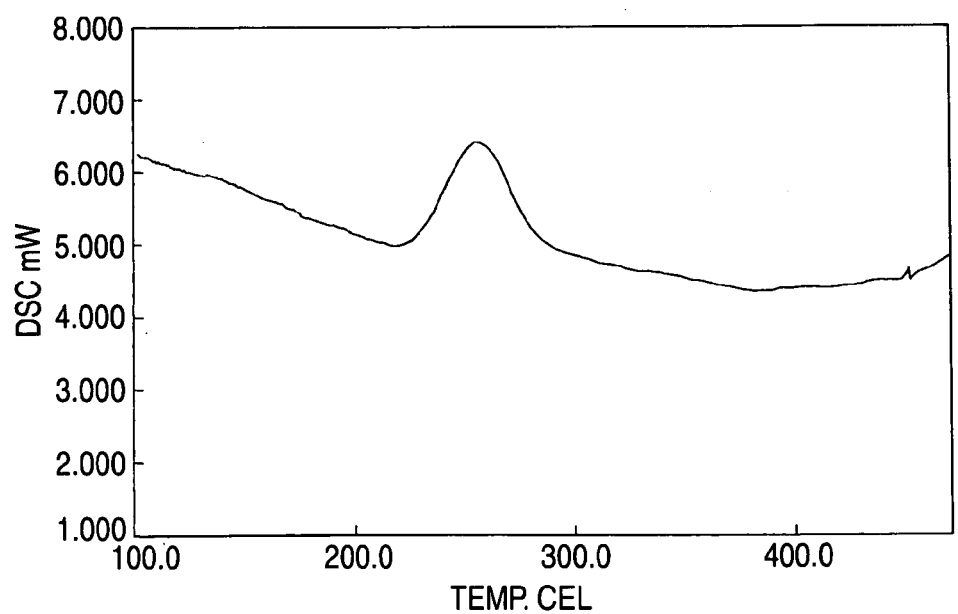
FIG. 2 is a view showing decomposition characteristics of the iridium compound obtained in Example 1.

The result of measuring decomposition characteristic of this compound is shown in FIG. 2. As is apparent from FIG. 2, the organometallic iridium compound of the present invention has a decomposition initiation temperature in the vicinity of 220° C., and therefore can be decomposed at lower temperature than the compound (conventional compound) obtained in Comparative Example 1 described hereinafter.

The measurement conditions are as follows.

Measurement method: Power compensation differential scanning calorimetry (DSC)

Measurement conditions:

Reference: Alumina

Inert gas: Nitrogen, 50 ml/min

Temperature rising: 10° C./min

Comparative Example 1

Figure 3:
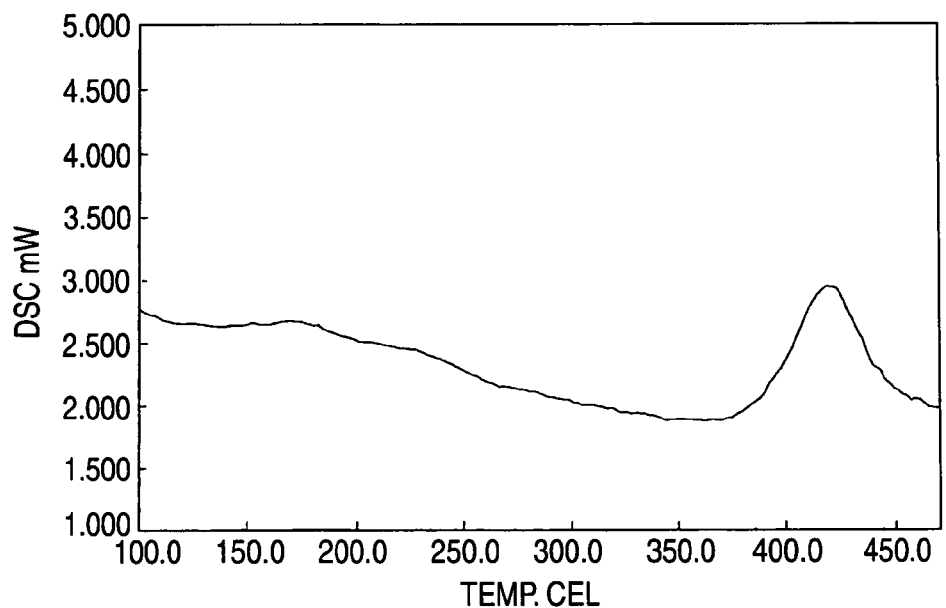
FIG. 3 is a view showing decomposition characteristics of (1,5-cyclooctadiene)(ethylcyclopentadienyl)iridium obtained in Comparative Example 1.

Thermal Decomposition Characteristic of (ethylcyclopentadienyl)(1,5-cyclooctadiene)iridium:

Decomposition characteristic of (ethylcyclopentadienyl)(1,5-cyclooctadiene)-iridium (conventional compound) was measured in the same manner as in Example 1. The result obtained is shown in FIG. 3. As is apparent from FIG. 3, this conventional product has a decomposition initiation temperature in the vicinity of 370° C.

Example 2

Synthesis of (methylcyclopentadienyl)bis(ethylene)iridium:

0.97 g of di μ-chlorotetrakis(ethylene)diiridium (I) was added to 50 ml of THF, and a reaction flask was cooled to −78° C., to which 50 ml of a THF solution of 178 mg of lithium methylcyclopentadienide was then added. The resulting mixture was stirred at −78° C. for 1 hour and 40 minutes, the temperature was then gradually elevated to room temperature, and the resulting mixture was further reacted for 1 hour, followed by concentration to obtain a muddy mixture. The muddy mixture was subjected to extraction with hexane, and the extract solution was subjected to column chromatography (eluant: hexane) using alumina to obtain 409 mg of the desired (methylcyclopentadienyl)bis(ethylene)iridium.

Figure 4:
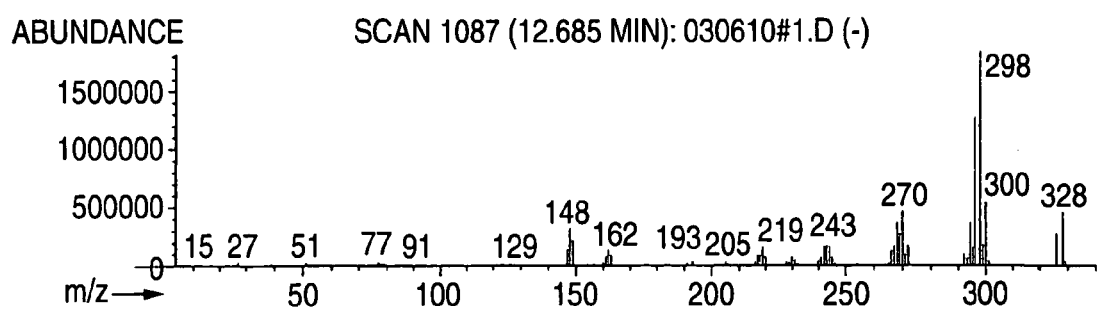
FIG. 4 is a view showing GC/MS chart of (methylcyclopentadienyl)bis-(ethylene)iridium obtained in Example 2.

Milky White Solid $^1$H-NMR (500 MHz, Benzene-d6, δ ppm): 4.84 (t, J=2.0 Hz, 2H), 4.59 (t, J=2.0 Hz, 2H), 2.55-2.44 (m, 4H), 1.51 (s, 3H), 0.95-0.93 (m, 4H) MS (GC/MS, EI): Molecular ion peak of (methylcyclopentadienyl)bis(ethylene)iridium in terms of $^{193}$Ir: m/z 328 (FIG. 4)

Example 3

Figure 5:
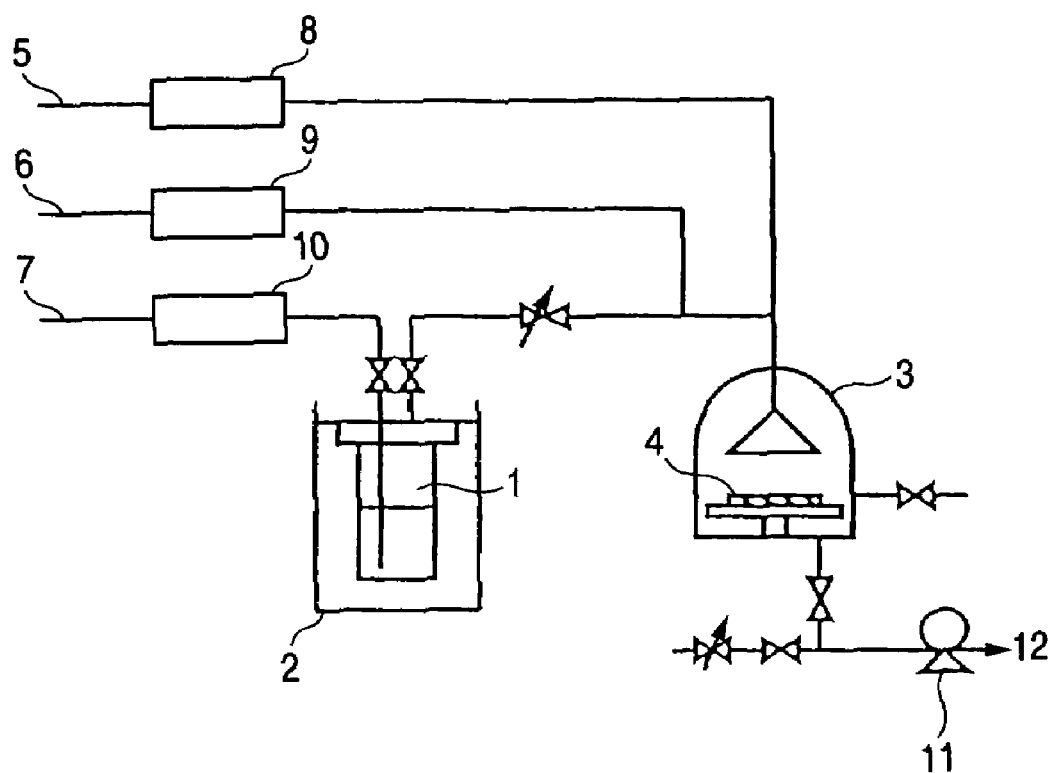
FIG. 5 is a schematic view of an equipment of the CVD process used in Example 3.

Production of Iridium Film using (ethylcyclopentadienyl) bis(ethylene)iridium:

An equipment shown in FIG. 5 was used, and a Si substrate in which a SiO$_2$ film of 100 nm had been formed on the surface thereof was used as a substrate 4. About 10 g of (ethylcyclopentadienyl)bis(ethylene)iridium was charged in a precursor container 1, and the container was heated with an oil bath 2 to make 50° C. constant temperature state. Using a vacuum pump 11 and pressure control valves, a reaction chamber 3 was adjusted at 10 Torr, and the precursor container 1 was adjusted at 100 Torr. Nitrogen was used as a carrier gas 7, and its flow rate was set up at 100 sccm by a mass flow controller 10. Oxygen was used as an oxidation gas 5, and nitrogen was used as a counter gas 6. The flow rate of the oxidation gas was set up at 10 sccm by a mass flow controller 8, and the flow rate of the counter gas was set up at 90 sccm by a mass flow controller 9. The substrate 4 was set up at 400° C., and subjected to film formation for 60 minutes while maintaining the heated state. The film formed was metallic iridium film, and its film thickness was 300 nm.

Although the present invention is described in detail and by reference to the specific embodiments, it is apparent to one skilled in the art that various modifications or changes can be made without departing the spirit and scope of the present invention.

This application is based on Japanese Patent Application No. 2003-295329 filed Aug. 19, 2003, No. 2003-383169 filed Nov. 12, 2003, and No. 2004-5503 filed Jan. 13, 2004, the disclosures of which are incorporated herein by reference in their entireties.

INDUSTRIAL APPLICABILITY

The organometallic iridium compounds of the present invention are liquid under gas bubbling conditions in the case of using CVD process as a process for preparing iridium-based films, so that those can quantitatively be supplied. Furthermore, the organometallic iridium compounds can be thermally decomposed at a temperature lower than that in the conventional materials. As a result, an iridium-based film having excellent step coverage can be formed on a substrate. The present invention makes it possible to prepare iridium-based films having excellent mass-productivity.

The invention claimed is:

1. An organometallic iridium compound represented by the following general formula (1):

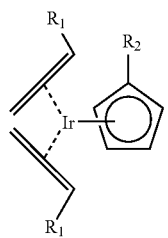

(1)

wherein $R_1$ represents hydrogen atom or a lower alkyl group; and $R_2$ represents a lower alkyl group.

2. The organometallic iridium compound as claimed in claim 1, wherein $R_1$ is hydrogen atom.

3. A process for producing the organometallic iridium compound as claimed in claim 1 or 2, which comprises reacting a compound represented by the following general formula (4):

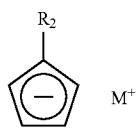

(4)

wherein $R_2$ represents a lower alkyl group, and M represents an alkali metal with a compound represented by the following general formula (2) or a compound represented by following general formula (3):

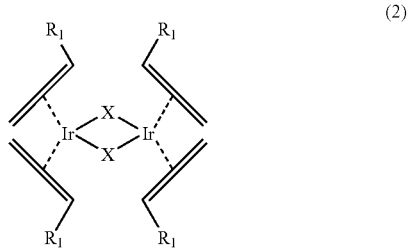

(2)

wherein $R_1$ represents hydrogen atom or a lower alkyl group, and X represents a halogen atom,

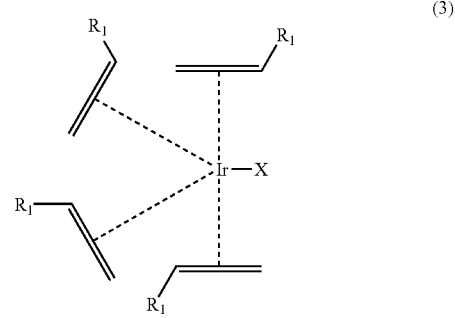

(3)

wherein $R_1$ and X are the same as defined above.

4. The process as claimed in claim 3, wherein $R_1$ is hydrogen atom.

5. A process for preparing iridium-based films, which comprises using, as a precursor, the organometallic iridium compound as claimed in claim 1 or 2.

6. The process as claimed in claim 5, wherein $R_1$ is hydrogen atom.

* * * * *